United States Patent [19]

Kitaoka et al.

[11] Patent Number: 5,342,343
[45] Date of Patent: Aug. 30, 1994

[54] DISPOSABLE TRAINING PANTS

[75] Inventors: Hideaki Kitaoka, Funabashi; Tohru Sasaki, Kawanoe, both of Japan

[73] Assignee: Uni-Charm Corporation, Ehime, Japan

[21] Appl. No.: 202,007

[22] Filed: Feb. 25, 1994

Related U.S. Application Data

[63] Continuation of Ser. No. 95,336, Jul. 23, 1993, abandoned, which is a continuation of Ser. No. 933,224, Aug. 21, 1992, abandoned.

[30] Foreign Application Priority Data

Aug. 28, 1991 [JP]  Japan ................................ 3-242776

[51] Int. Cl.$^5$ ............................................. A61F 13/15
[52] U.S. Cl. ............................ 604/385.2; 604/385.1; 604/378; 604/358
[58] Field of Search ............... 604/358, 367, 378–385.2

[56] References Cited

U.S. PATENT DOCUMENTS 3,994,299  11/1976  Karami .
4,940,464  7/1990   Van Gompel .
4,960,414  10/1990  Meyer .
5,062,839  11/1991  Anderson .

FOREIGN PATENT DOCUMENTS 2023067  12/1979  United Kingdom .
2244201  11/1991  United Kingdom .
9111161  8/1991   World Int. Prop. O. .

Primary Examiner—Randall L. Green
Assistant Examiner—Rob Clarke
Attorney, Agent, or Firm—Fred Philpitt

[57] ABSTRACT

Disposable training pants improved for effectively making babies wearing the training pants aware of their own excretions. There are provided on a topsheet of the pants a moistness holding sheet 11 having floating zones 11a serving as moistness sensor means.

5 Claims, 1 Drawing Sheet

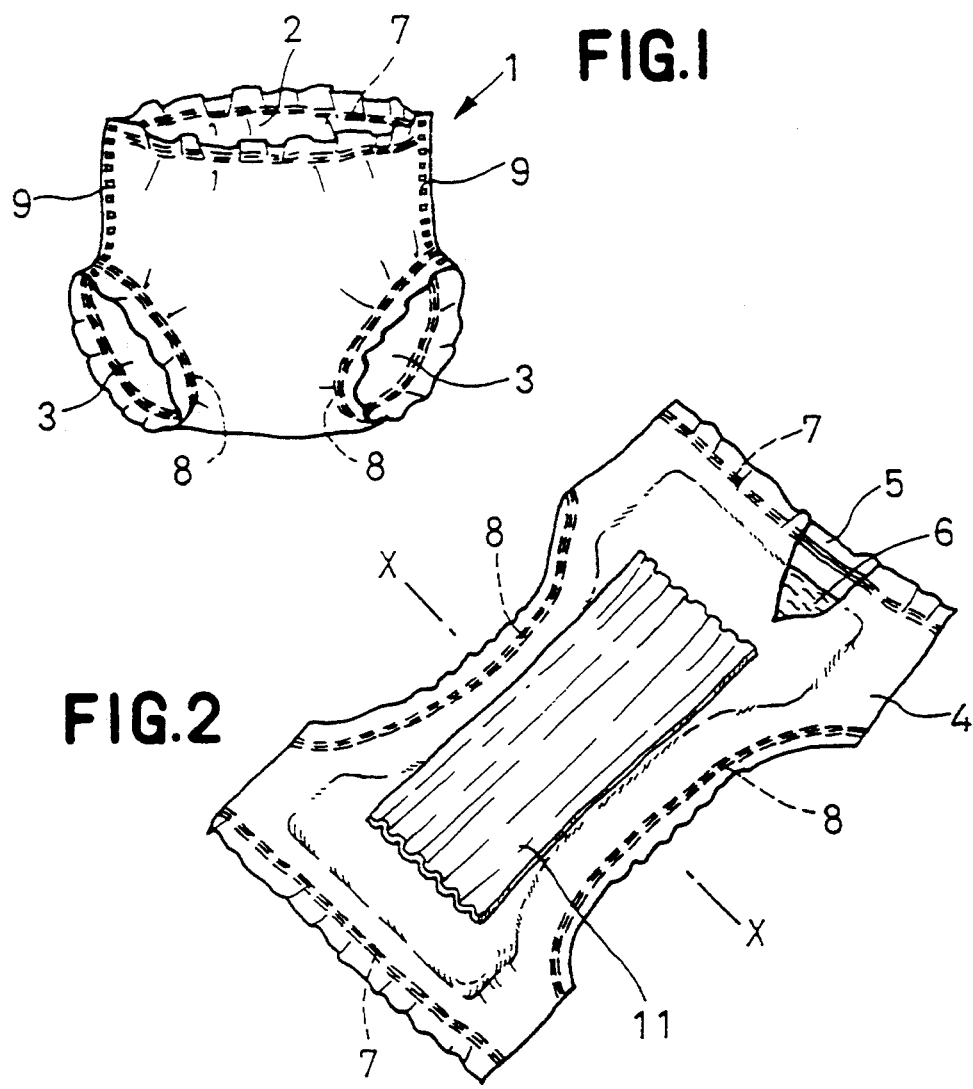
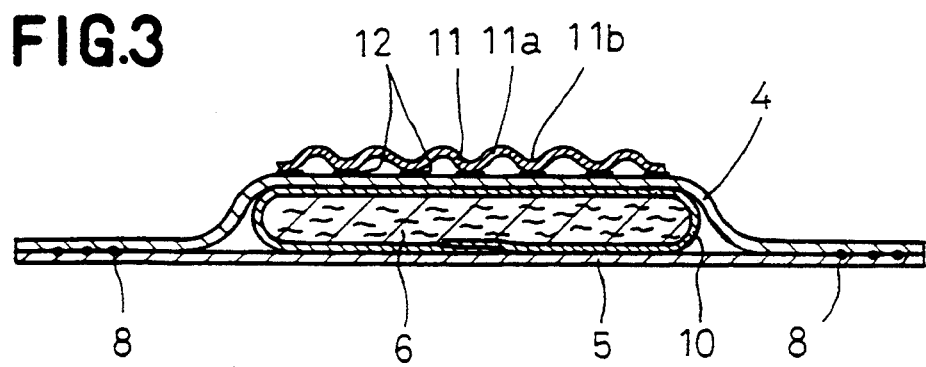

DISPOSABLE TRAINING PANTS

This is a continuation of patent application Ser. No. 08/095,336 filed Jul. 23, 1993 now abandoned, which is a continuation of patent application Ser. No. 07/933,224 filed Aug. 21, 1992 now abandoned.

BACKGROUND OF THE INVENTION

The present invention relates to disposable training pants and more particularly to so-called training pants used for training babies to acquire a habit of living without diapers as early as possible.

The conventional training pants are generally made of cloth and reused after washed. When a baby excretes with such pants put on, a quantity of liquid excretions readily leaks from the pants. Consequently, babies feel uncomfortable and tell their mothers about the excretions.

However, such training pants are disadvantageous not only in that these training pants require washings but also in that carpets or the like on floor are often contaminated by the quantity of excretions leaked from the pants.

Accordingly, it is a principal object of the invention to provide the pants so improved to be free from leakage of liquid excretions which have been inevitable for the conventional pants made of cloth, on one hand, and to be effective in making babies aware of the pants having been wetted with excretions, on the other hand.

SUMMARY OF THE INVENTION

The object set forth above is achieved, according to the invention, by disposable training pants comprising a liquid-permeable topsheet, a liquid-impermeable backsheet and a liquid absorbent core sandwiched between the top- and backsheets and having a waist-opening and a pair of leg-openings, both of the waist-opening and leg-openings being provided with stretchable elastic members, respectively, the disposable training pants being characterized by that a moistness holding sheet is partially bonded to the topsheet at least over a central zone thereof so that the moistness holding sheet partially floats above the topsheet.

Preferably, the moistness holding sheet comprises nonwoven fabric primarily made of hydrophilic fiber. Alternatively, the moistness holding sheet may be made of soft spongy material. The topsheet has a stretchable elasticity and the floating zones are formed by partially bonding the moistness holding sheet to the topsheet while the topsheet is being stretched.

With the training pants of this invention constructed as mentioned above, fluid excretions are first absorbed by the moistness holding sheet and a quantity of such fluid excretions once absorbed into the floating zones of the moistness holding sheet are substantially free form direct absorbing action of the core sandwiched between the top and backsheets, so the quantity of fluid excretions substantially remain in the floating zones. Thus, these floating zones make babies aware of moistness.

BRIEF DESCRIPTION OF THE DRAWINGS

The training pants of the invention will now be described, by way of example, with reference to the attached drawings, in which:

FIG. 1 is a perspective view an embodiment of the training pants constructed according to the invention;

FIG. 2 is a perspective view showing an inner side of said pants as unfolded and partially broken away; and FIG. 3 is an enlarged sectional view taken along a line X—X in FIG. 2.

DESCRIPTION OF THE PREFERRED EMBODIMENTS

Referring to FIGS. 1 through 3, pants 1 have a waist-opening 2 and a pair of leg-openings 3. The pants 1 comprise a liquid-permeable topsheet 4, a liquid-impermeable backsheet 5 and a sheet- or mat-like liquid absorbent core 6 sandwiched between the top- and backsheets. Stretchable elastic members 7, 8 are bonded with adhesive under their stretched condition between zones of the top- and backsheets 4, 5 defining the waist-opening 2 and the leg-openings 3, respectively. Components of the pants 1 are laminated with the topsheet 4 lying on the inner side as viewed in the unfolded condition as seen in FIG. 2. This laminate is longitudinally folded in two and intermittently welded together along opposite sides leaving the respective leg-openings 3 unwelded. A moistness holding sheet 11 is bonded to the topsheet 4 at least over a central zone thereof.

The topsheet is nonwoven fabric made of thermoplastic, hydrophobic crimped fibre such as polypropylene or polyester, or such fibre mixed, if desired, with suitable hydrophilic fibre, for example, rayon or acetate fibre of 0 to 50% by weight and, in any case, subjected to the fluid-jet entangling or intertwining process so as to form a sheet which is stretchable both in length and width and has a unit weight of 25 to 45 $g/m^2$, an apparent bulkiness of 0.2 to 0.7 mm and a density of 0.06 to 0.12 $g/cm^3$. The backsheet 5 consists of liquid-permeable nonwoven fabric substantially similar to the topsheet 4 and being also stretchable both in length and width, on one hand, and moistness-permeable film made of plastic or elastomeric material which is also stretchable both in length and width and integrally bonded to said nonwoven fabric, on the other hand. Alternatively, the backsheet may comprise liquid-impermeable or liquid-resistant nonwoven fabric. The core 6 is made of a mixture of fluffy pulp, thermoplastic hydrophobic crimped fibre and super absorbent polymer powder, which are then molded into sheet or mat and then covered with water absorbent tissue paper 10.

The moistness holding sheet 11 is nonwoven fabric made of hydrophilic fibre such as rayon or acetate fibre (inclusive of surface-hydrophiled polyester fibre or the like) or such fibre mixed, if desired, with suitable thermoplastic hydrophobic fibre, for example, polypropylene or polyester fibre and, in any case, subjected to melt bond or fluid-jet entangling or intertwining process so as to form a sheet having a unit weight of 20 to 40 $g/m^2$, an apparent bulkiness of 0.2 to 1.0 mm and a density of 0.025 to 0.12 $g/cm^3$. The moistness holding sheet 11 preferably has a width of 40 to 100 mm and a length of 60 to 240 mm.

Principally, it depends on a desired relative control of wetting characteristic and permeability of the topsheet 4 as well as the moistness holding sheet 11 for excretions whether the nonwoven fabric used as the topsheet 4 should be made from hydrophobic fibre mixed with hydrophilic fibre or not, whether the nonwoven fabric used as the moistness holding sheet 11 should be made from hydrophilic fibre mixed with hydrophobic fibre or not and to what levels the unit weights, apparent bulkinesses and densities of the topsheet 4 and the moistness holding sheet 11 should be adjusted, respectively. Regarding the wetting characteristic, for example, the moistness holding sheet 11 preferably should have a wetting characteristic higher than that of the topsheet 4 in view of the particular function expected from this moistness holding sheet 11 and it has been found that the above-mentioned values are generally satisfactory to achieve the object of the invention without any significant increase of cost. It should be understood, however, that said values have been mentioned merely as exemplary values and the invention is not limited to these values.

Though not shown, the moistness holding sheet 11 may be formed from composite nonwoven fabric consisting of top layer having a relatively high fibre density and bottom layer having a relatively low fibre density or from nonwoven fabric having a fibre-fluffed bottom surface to achieve a further improved moistness holding effect. Alternatively, the moistness holding sheet 11 may be formed from a liquid-absorbent, soft spongy sheet of urethane, cellulose or the like having a thickness of 0.3 to 2 mm.

Before the moistness holding sheet 11 is laminated on the topsheet 4, the moistness holding sheet 11 is undulated to form floating zones (ridges) 11a and non-floating zones (grooves) 11b and the non-floating zones 11b are bonded to the topsheet 11 with bonding means 12 provided onto the corresponding zones of the topsheet 4. Such laminating may be achieved, for example, by bonding the moistness holding sheet 11 to the topsheet 4 which is being stretched in length and/or width. The floating zones 11a may be also arranged in a pattern of lateral stripes, scattered dots or the like, instead of the vertical stripes as shown. In any case, the floating zones 11a preferably lie at a height spaced above the upper surface of the topsheet 4 as far as possible and preferably has an occupation ratio with respect to the entire moistness holding sheet 11 as high as possible. More specifically, after the topsheet 4 has contracted, said height is preferably 1 mm or higher and said ratio is preferably 20% or higher. The topsheet 4 may be partially provided with the bonding means 12 on the zones depending on the particular pattern of the floating zones 11a. Bonding may be achieved by use of adhesive or welding.

With the training pants provided by the invention, a quantity of fluid excretions once absorbed into the floating zones of the moistness holding sheet is substantially free from direct absorbing action of the core sandwiched between the top- and backsheets, so said quantity of fluid excretions substantially remain in the floating zones which are normally in contact with babies' skins and make babies feel uncomfortable. Thus, babies are aware of their own excretions and acquire a habit of telling another person about excretions during use of the pants.

Furthermore, the floating zones of the moistness holding sheet project upward from the topsheet normally against babies' skins. This feature allows babies to be aware of moistness more sensibly than in the case having none of the floating zones even when the pants are not put on babies' bodies at a level sufficiently high to keep the topsheet in contact with babies' skins around the crotch area or even if the pants have been somewhat displaced with respect to said level.

While the moistness holding sheet is provided at a zone which is most apt to be exposed to excretions, sticking of excrement to babies' skins is effectively reduced as a secondary effect because such soft excrement flows from the floating zones down to the non-floating zones.

What is claimed is:

1. Disposable training pants for babies that have a waist opening, a pair of leg openings and stretchable elastic members surrounding said waist and leg openings, said pants comprising
    (a) a liquid-permeable topsheet (4),
    (b) a liquid-impermeable backsheet (5),
    (c) a liquid absorbent core (6) sandwiched between said topsheet (4) and said backsheet (5), and
    (d) a moistness holding sheet (11)
        (i) that is intermittently bonded to said topsheet (4) over a central portion of the topsheet (4) except for peripheral portions thereof which extend outwardly from the peripheral edges of said absorbent core so that the moistness holding sheet (11) has a plurality of raised portions extending above said topsheet (4) that are adapted to contact a baby's skin, and
        (ii) that has a wetting characteristics higher than that of said topsheet (4)
whereby when there is a liquid excretion into the training pants said raised portions of said moisture holding sheet (11) will retain a part of the liquid excretion and by being in contact with a baby's skin will make the baby aware of its own excretion.

2. Disposable training pants for babies that have a waist opening, a pair of leg openings and stretchable elastic members surrounding said waist and leg openings, said pants comprising
    (a) a liquid-permeable topsheet (4),
    (b) a liquid-impermeable backsheet (5),
    (c) a liquid absorbent core (6) sandwiched between said topsheet (4) and said backsheet (5), and
    (d) a moistness holding sheet (11) having a plurality of ridges (11a) and grooves (11b), said sheet
        (i) having the bottoms of its grooves (11b) bonded to said topsheet (4) over a central portion of the topsheet (4) so that the ridges (11a) of the moistness holding sheet (11) are spaced above said topsheet (4) and are adapted to contact a baby's skin, and
        (ii) having a wetting characteristics higher than that of said topsheet (4)
whereby when there is a liquid excretion into the training pants said ridges (11a) of said moisture holding sheet (11) will retain a part of the liquid excretion and by being in contact with a baby's skin will make the baby aware of its own excretion.

3. Training pants as recited in claim 2, wherein said moistness holding sheet (11) comprises nonwoven fabric composed primarily made of hydrophilic fibers.

4. Training pants as recited in claim 2 wherein said moistness holding sheet (11) is made of soft spongy material.

5. Training pants as recited in claim 2 wherein said topsheet (4) has a stretchable elasticity and wherein said ridges (11a) are formed by partially bonding said moistness holding sheet (11) to said topsheet (4) while said topsheet (4) is being stretched.

* * * * *